US008545230B2

(12) United States Patent
Stalling et al.

(10) Patent No.: US 8,545,230 B2
(45) Date of Patent: Oct. 1, 2013

(54) METHOD AND APPARATUS FOR A NON-NUTRITIVE SUCK ENTRAINMENT PULSE GENERATOR

(75) Inventors: David L. Stalling, Lenexa, KS (US); Mike Litscher, Lenexa, KS (US)

(73) Assignee: Innara Health, Inc., Shawnee, KS (US)

( * ) Notice: Subject to any disclaimer, the term of this patent is extended or adjusted under 35 U.S.C. 154(b) by 968 days.

(21) Appl. No.: 12/564,802

(22) Filed: Sep. 22, 2009

(65) Prior Publication Data

US 2010/0075285 A1      Mar. 25, 2010

Related U.S. Application Data

(60) Provisional application No. 61/098,988, filed on Sep. 22, 2008.

(51) Int. Cl.
*G09B 19/00* (2006.01)

(52) U.S. Cl.
USPC .......................................................... 434/258

(58) Field of Classification Search
USPC .......................................................... 434/258
See application file for complete search history.

(56) References Cited

U.S. PATENT DOCUMENTS

| 4,170,971 | A | * | 10/1979 | Yamanaka et al. | 123/327 |
| 4,941,469 | A | * | 7/1990 | Adahan | 128/205.18 |
| 5,474,683 | A | * | 12/1995 | Bryant et al. | 210/646 |
| 5,931,929 | A | * | 8/1999 | Tran et al. | 710/69 |
| 2006/0079814 | A1 | * | 4/2006 | Barlow et al. | 600/590 |
| 2009/0222214 | A1 | * | 9/2009 | Barlow et al. | 702/19 |

FOREIGN PATENT DOCUMENTS

| CN | 102209516 A | 10/2011 |
| WO | WO-2010033252 A1 | 3/2010 |

OTHER PUBLICATIONS

"International Application Serial No. PCT/US2009/005263, Search Report mailed Jan. 12, 2010", 3 pgs.
"International Application Serial No. PCT/US2009/005263, Written Opinion mailed Jan. 12, 2010", 5 pgs.
Barlow, S M, et al., "Synthetic orocutaneous stimulation entrains preterm infants with feeding difficulties to suck", Joural of Perinatology, 2008, (28), (Aug. 2008), 541-548.
"European Application Serial No. 09789360.6, Office Action mailed Apr. 10, 2012", 4 pgs.
"European Application Serial No. 09789360.6, Response filed Aug. 17, 2012 to Examination Notification Art. 94(3) mailed Apr. 10, 2012", 14 pgs.

* cited by examiner

*Primary Examiner* — Xuan Thai
*Assistant Examiner* — Jerry-Daryl Fletcher
(74) *Attorney, Agent, or Firm* — Schwegman Lundberg & Woessner, P.A.

(57) ABSTRACT

This document discusses, among other things, method and apparatus for a non-nutritive suck (NNS) entrainment pulse generator. An embodiment includes a valve assembly in communication with a first pressure and a second pressure to change a pressure of a baglet. A controller can switch the valve assembly to selectively couple the first and second pressures to the baglet to produce a series of pressure pulses within the baglet. In an embodiment, the pulse generator is substantially self-contained. In an embodiment, the valve assembly includes a reciprocating piston assembly to generate the series of pressure pulses. In an embodiment, the NNS entrainment pulse generator is portable.

20 Claims, 6 Drawing Sheets

METHOD AND APPARATUS FOR A NON-NUTRITIVE SUCK ENTRAINMENT PULSE GENERATOR

CLAIM OF PRIORITY

This application claims the benefit under 35 U.S.C 119(e) of U.S. Provisional Application Ser. No. 61/098,988 filed Sep. 22, 2008 and which is hereby incorporated by reference in its entirety.

TECHNICAL FIELD

This patent application relates generally to method and apparatus for development of infant oromotor behavior, and more particularly to method and apparatus for a non-nutritive suck entrainment pulse generator.

BACKGROUND

Sucking is a precocial motor behavior in humans. However, premature infants often demonstrate oromotor dyscoordination and are unable to suck or feed orally. This inability to feed can delay discharge from neonatal intensive care units and hinder development of coordinated oromotor behavior.

Infants' readiness to feed is often evaluated by their display of non-nutritive sucking (NNS). Typically, NNS begins between 28 and 33 weeks gestational age (GA) and is remarkably stable by 34 weeks.

The brain of a typically developing fetus includes an organized set of neurons in the brainstem and cortex that are involved in the production of centrally patterned rhythmic motor behaviors. These neural circuits are known as central pattern generators or simply "CPG's". One such rhythmic behavior that is controlled by a CPG is the suck. Under normal circumstances, the human infant is precocial for suck, which means it is a motor behavior that is established in utero and functional at birth. An infant's ability to suck at birth is important for, among other things, getting nourishment and stimulating the infant's developing brain.

In premature birth, the premature infant loses opportunities for safe neurological development in utero. This loss can be compounded by medical complications associated with premature birth, such as strokes or hemorrhages. Further, medical complications often are treated with painful procedures which correlate with impairment in neurological development. As a result of the impairment in neurological development, the premature infant may possess grossly disorganized CPG's and therefore exhibit grossly disorganized suck, which itself can lead to other medical complications and a failure to thrive and develop. Other ramifications of disorganized suck may include: ramifications relating to the infant's overall sensorimotor development, perceptual capacity, and even delays in higher cognitive function including speech, language, and other processing skills. There is a need in the art for devices to assist development of organized suck patterns in patients exhibiting disorganized suck.

SUMMARY

The present disclosure includes apparatus and methods for a non-nutritive suck (NNS) entrainment pulse generator for developing organized non-nutritive suck in infants. In one embodiment, a NNS entrainment pulse generator includes a valve assembly in communication with a first pressure and a second pressure. A controller, coupled to the valve assembly, provides a series of pressure pulses within a baglet. The baglet may be used to entrain non-nutritive suck (NNS) of an infant. In one embodiment the first and second pressures are coupled directly to the baglet. In various embodiments, a NNS entrainment pulse generator is portable to allow for home use and to reduce patient traffic in hospitals and clinics. In an embodiment, the pulse generator includes chambers for the pressure sources and is substantially self contained to further enhance portability In one embodiment, a non-nutritive suck entrainment pulse generator includes a reciprocating piston assembly to produce the series of pressure pulses. The reciprocating pistons are driven using the first and second pressures. In one embodiment, the reciprocating pistons are driven using a vacuum source and atmospheric pressure. In one embodiment, the reciprocating pistons are driven using a positive pressure source and atmospheric pressure. The baglet couples to the ends of a cylinder housing the pistons, The baglet expands and contracts as the pistons move away from each other, and then toward each other, respectively.

This Summary is an overview of some of the teachings of the present application and not intended to be an exclusive or exhaustive treatment of the present subject matter. Further details about the present subject matter are found in the detailed description. The scope of the present invention is defined by the appended claims and their legal equivalents.

DETAILED DESCRIPTION

The following detailed description of the present subject matter relates to the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
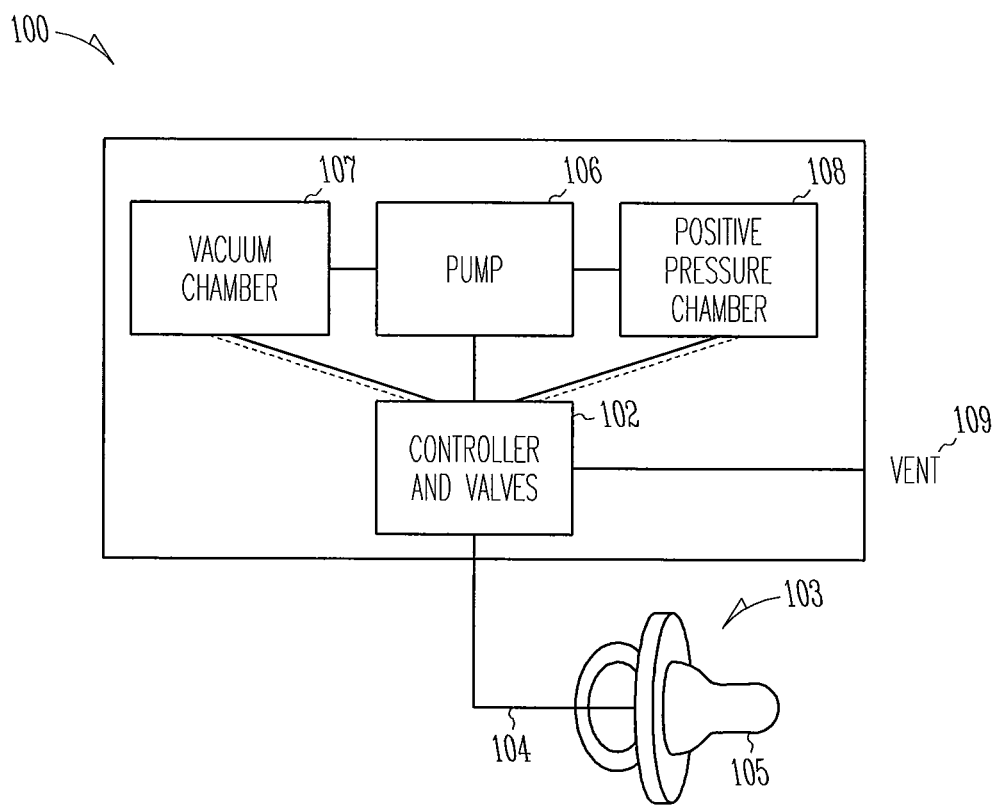
FIG. 1 shows a substantially self-contained, non-nutritive suck (NNS) entrainment pulse generator apparatus, according to one embodiment of the present subject matter.

FIG. 1 shows a substantially self-contained, non-nutritive suck (NNS) entrainment pulse generator apparatus 100 according to one embodiment of the present subject matter. The apparatus 100 includes a pneumatically actuated patient therapy handpiece, or pacifier assembly 103 for delivering oral entrainment therapy to a patient. A controller 102 actuates valves in a pneumatic circuit to generate a series of positive and negative pneumatic pulses thru a tube 104 coupling the circuit to the pacifier assembly 103. The controller 102 also controls a pump 106 connecting a vacuum, or negative pressure chamber 107, and a positive pressure chamber 108. The vacuum chamber and positive pressure chamber provide the pneumatic pressure sources for the pressure pulses. A vent 109 allows adjustment of pressure and vacuum for different therapy regiments. The vent 109 also allows adjustment of the system for pneumatic losses.

The nipple 105, or baglet, of the pacifier assembly 103, functions as an expandable membrane made from a suitable inert elastomer such as medical grade silicone. The pressure pulses expand and contract the nipple 105. When the nipple of the pacifier assembly 103 is in a patient's mouth, the nipple's expansion and contraction is detected by a neural sensory network in the patient's lips, tongue and mouth. With regimented application of the pressure pulses, the suck central pattern generator (CPG) of the patient's brain can be modulated and subsequently entrained with an organized suck pattern. The self contained nature and portability of the apparatus expands the potential for consistent and timely success of entrainment therapy over existing therapy systems as existing therapy systems are large and cumbersome to move. The present subject matter allows therapy to be easily delivered at home, as well as, other locations remote from the traditional setting of a hospital or a clinician's office. In a hospital environment, the portability allows the equipment to be brought to the patient room reducing patient traffic thru the hospital. In some embodiments, the apparatus includes a rechargeable battery to provide power for operating the apparatus in a stand-alone mode.

Figure 2:
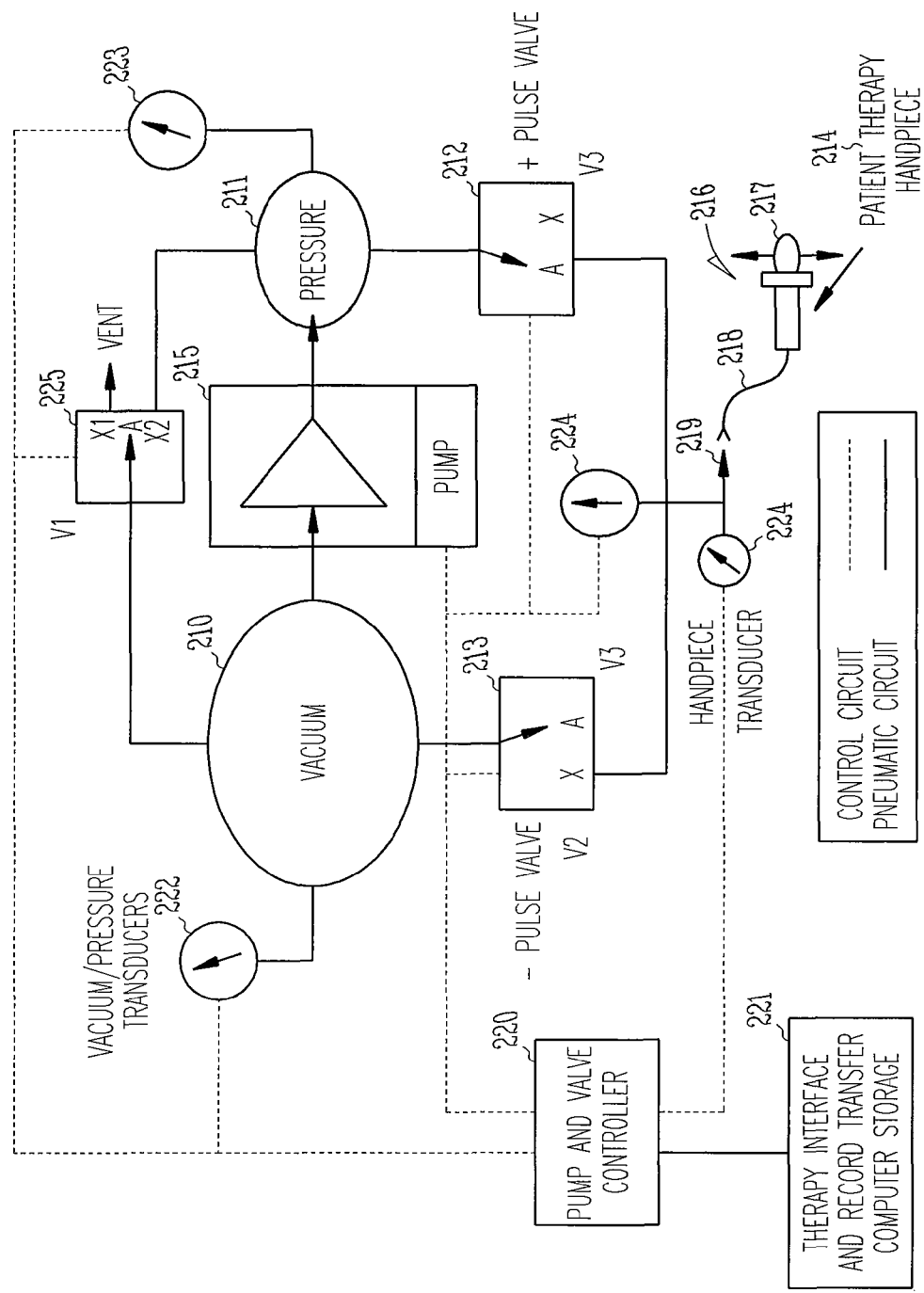
FIG. 2 shows a block diagram of a NNS entrainment pulse generator apparatus, according to one embodiment of the present subject matter.

FIG. 2 shows a block diagram of a NNS entrainment pulse generator apparatus according to one embodiment of the present subject matter. The apparatus includes a vacuum, or negative pressure, chamber 210, a pressure chamber 211, a positive pulse valve 212, a negative pulse valve 213, a pacifier assembly 214 and a pump 215. The vacuum 210 and pressure 211 chambers provide the pneumatic pressure sources for delivering stimulation pressure pulses to the pacifier assembly 214. Each chamber is connected to the pacifier assembly through a pneumatic valve. The vacuum chamber 210 is connected to the pacifier assembly 214 through a negative pulse valve 213 and the positive pressure chamber 211 is connected to the pacifier assembly 214 through the positive pulse valve 212. The pump 215 transfers gas from the vacuum chamber 210 to the positive pressure chamber 211. With proper sizing of the respective chambers, the system becomes a substantially closed pneumatic system. As such, the transfer of gas from the vacuum chamber 210 into the positive pressure chamber 211 develops adequate vacuum and pressure to provide NNS entrainment therapy using the pacifier assembly 214. The pacifier assembly 214 includes a pacifier 216 having a nipple 217, or baglet, and tubing 218 to connect the nipple 217 to the pneumatic circuit of the apparatus. In various embodiments, the pacifier assembly 214 includes one or more pneumatic connectors 219 to allow easy replacement of the pacifier assembly 214.

The apparatus includes a controller 220 to monitor the pump and valves, and sequence the pump and valves to deliver the NNS entrainment therapy. A port 221 connected to the controller 220 provides an interface to connect a computer and transfer data between the controller and the computer. In various embodiments, the controller 220 includes memory for recording data during application of entrainment therapy. Data recorded into the computer memory and available for exchange to a device connected to the port includes, but is not limited to, data received from various apparatus transducers, status of controller inputs and outputs, including outputs connected to the control valves, and status information native to the controller such as therapy parameters and controller status data.

Transducers are connected to the controller 220 to provide pressure feedback to the controller. The illustrated embodiment includes a vacuum chamber transducer 222, a positive pressure chamber transducer 223 and one or more pacifier assembly transducers 224. In various embodiments, one pacifier assembly transducer 224 connects to the pneumatic circuit at or near the outputs of the control valves and a second pacifier assembly transducer is connected near the pacifier of the pacifier assembly. Monitoring the two transducers can help identify pneumatic problems in the pneumatic circuit. In various embodiments, the controller is programmable and includes parameters to define maximum pressure and minimum vacuum levels for the NNS entrainment therapy pulses as well as issues with the application of the therapy. The transducers allow the controller 220 to control the pump 215 more accurately than in an open loop mode to attain adequate vacuum and pressure levels in the respective chambers and to record and monitor the delivered therapy while the therapy is applied. In various embodiments, leakage and/or changes in programmed therapy pressure levels require venting pressure from the pressure chamber 211 to the vacuum chamber 210 or exposing the vacuum chamber 210 to atmospheric pressure. The illustrated embodiment includes a 3-position pneumatic adjustment valve 225 electrically connected to the controller and pneumatically coupled to the vacuum chamber, the positive pressure chamber and the atmosphere. In a first default state (A), the valve 225 does not connect any of the pneumatic pathways to each other. In a second state, or valve position (X1), the valve connects the vacuum chamber 210 to the atmosphere. In a third state (X2), the valve connects the positive pressure chamber 211 to the vacuum chamber 210. It is understood that other valves and valve configurations are possible without departing from the scope of the present subject matter.

Sequentially coupling the positive pressure 211 and vacuum 210 chambers to the pacifier assembly 214 using the positive 212 and negative 213 pulse valves applies pressure waves to the pacifier assembly 214. The negative pulse valve 213 has two states, or valve positions. A first state (X) of the negative pulse valve 213 couples the vacuum chamber 210 to the pacifier assembly 214 evacuating pressure from the pacifier assembly nipple 217. A second state (A) isolates the vacuum chamber 210 from the pacifier assembly 214. The positive pulse valve 212 has two states, or valve positions. A first state (A) of the positive pulse valve couples the positive pressure chamber 211 to the pacifier assembly 214 inflating the pacifier assembly nipple 217. A second state (X) of the positive pulse valve 212 isolates the positive pressure chamber 211 from the pacifier assembly 214. It is understood that other valves and valve configurations are possible without departing from the scope of the present subject matter.

The configuration of the substantially closed, pressure pulse generator avoids issues with muffling exhaust pulses as well as the accumulation of condensation from compressing non-dehumidified room air.

Sizing of the apparatus components depends on the desired pressure, frequency and duration of the pressure pulses. For example, a system with a hand piece nipple and connecting tube with total volume less than 5 milliliters, delivering 6 pressures pulses at a frequency of 1.8 hertz and a 2 second rest pause for every 10 seconds of applied therapy and producing a change of pressure inside the nipple from atmospheric to ±100 cm $H_2O$, requires a minimum pumping capacity of approximately 75 ml of air per minute to effect 32 positive pulses and 32 negative pulses where the maximum positive pulse pressure is approximately 2 psi. The corresponding valves and air lines are sized to provide at least 100 ml/min of gas flow assuming some efficiency loss due to flow restrictions. The corresponding valves require a minimum rise time of 10 ms to achieve the pressure increase rise time to generate impulse motion for creating neurological stimulus.

At startup, the controller 220 activates the pump and configures the external pneumatic circuit leading to the pacifier assembly 214 such that the negative pulse valve and the positive pulse valve isolate the pacifier assembly from the vacuum chamber and the positive pressure chamber until the operating vacuum and pressure are reached. The volume ratio of the two pressure reservoirs is selected such that displacement of most of the air from the vacuum chamber (~500 mL) into the positive pressure chamber provides at least 250 cm $H_2O$ pressure (assuming that a large fraction of the air in the vacuum reservoir is transferred to the pressure reservoir ~100 mL). A working positive pressure of ~200 cm $H_2O$ produces and sustains the 100 cm $H_2O$ pressure maximum of the pressure pulse. The pumping capacity of the pump required is approximately 250 mL/min. In various embodiments, the pumping capacity is provided using a 12 VDC motor driven diaphragm pump. It is understood that other pump and motor configurations are possible without departing from the scope of the present subject matter.

Figure 3A:
FIGS. 3A and 3B show alternating pressure pulse waveforms recorded from an NNS entrainment apparatus, according to one embodiment of the present subject matter.
Figure 3B:
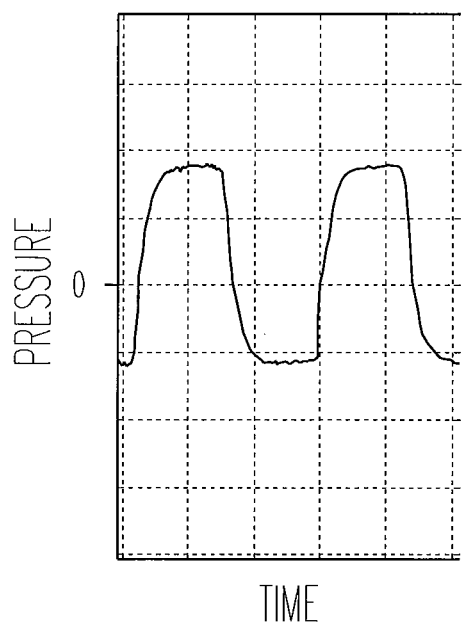

FIGS. 3A and 3B show alternating pressure pulse waveforms recorded from an NNS entrainment apparatus according to one embodiment of the present subject matter. FIG. 3A is a recording of the pressure waveform near the output of the control valves. FIG. 3B is a recording of the pressure waveform near the pacifier assembly. Note that the sharpness of the pulses is attenuated in the waveform recorded near the pacifier assembly. The rise time of the pulses is affected by the volume of the pacifier assembly nipple and the size, shape and material of the couplings and tubing connecting the pacifier assembly to the control valves. In general, less restrictive materials and larger tubing will produce faster rise times in the waveform.

Figure 4:
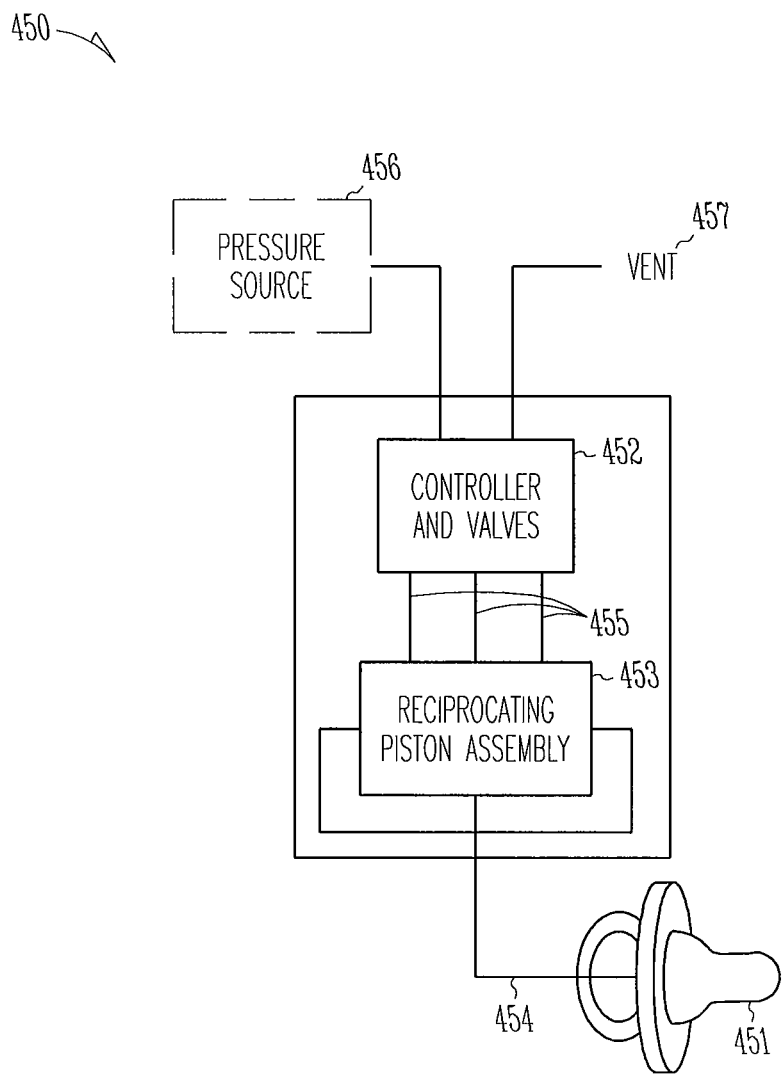
FIG. 4 shows a block diagram of a NNS entrainment pulse generator apparatus, according to one embodiment of the present subject matter.

FIG. 4 shows a block diagram of a NNS entrainment pulse generator 450 apparatus according to one embodiment of the present subject matter. The apparatus 450 includes a pneumatically actuated pacifier assembly 451 for delivering oral entrainment therapy to a patient. A controller 452 actuates valves to actuate a reciprocating piston assembly 453 to generate a series of positive and negative pneumatic pulses thru tubing 454 coupling the circuit to the pacifier assembly 451. The control valves couple and decouple ports 455 on the reciprocating piston assembly to a pressure source 456 and a vent 457 to generate the pressure pulses. In various embodiments, the pressure source is a positive pressure source. In some embodiments, the pressure source is a vacuum, or negative pressure source.

Figure 5A:
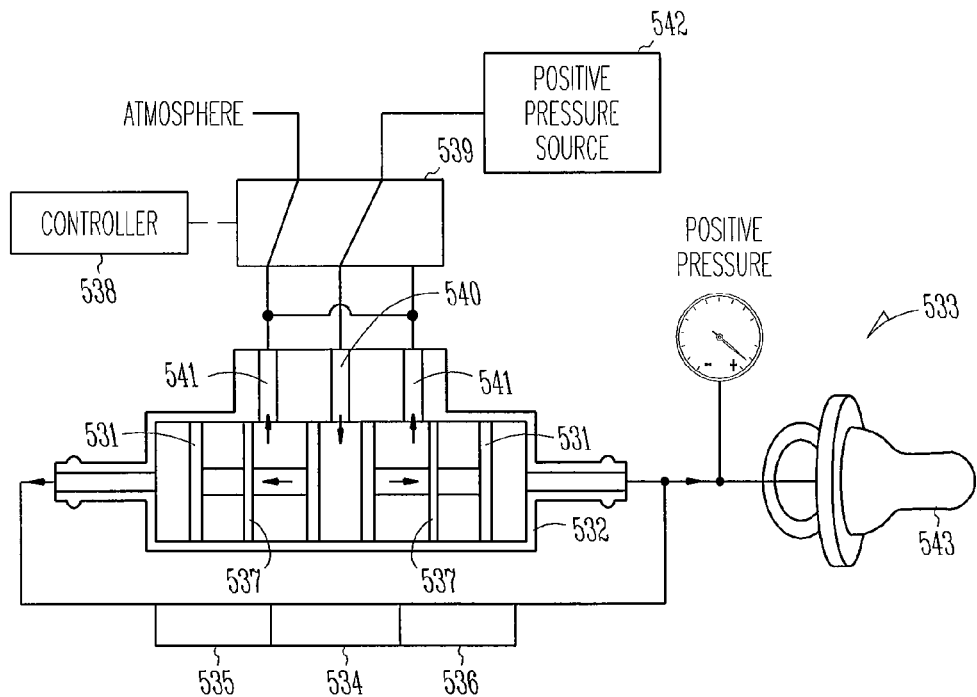
FIGS. 5A and 5B show a NNS entrainment apparatus with a reciprocating piston pulse generator, according to one embodiment of the present subject matter.
Figure 5B:
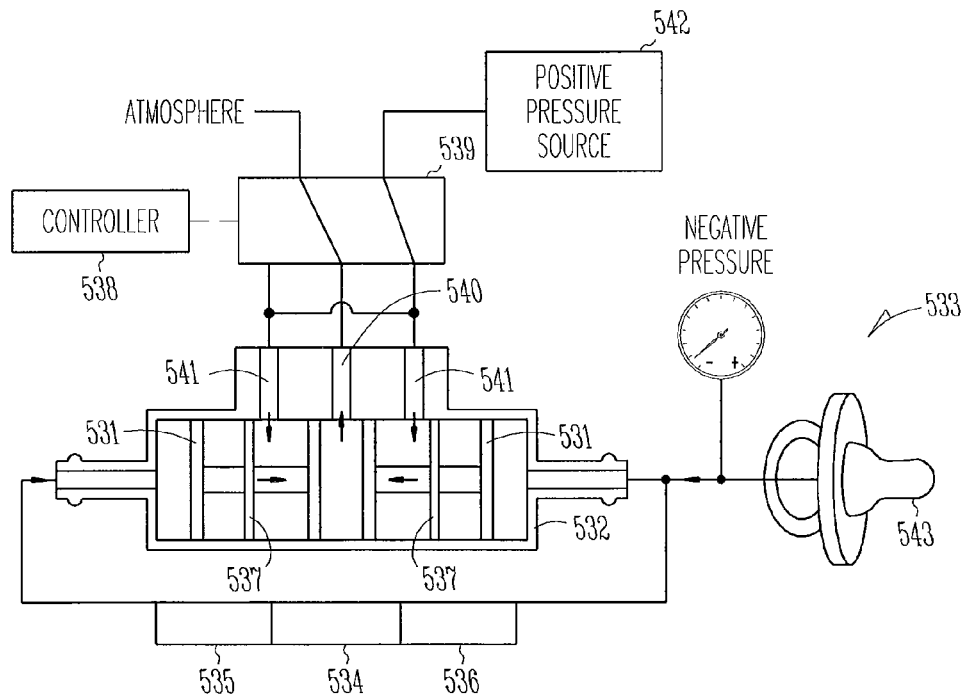

FIGS. 5A and 5B show a NNS entrainment apparatus with a reciprocating piston pulse generator according to one embodiment of the present subject matter. The apparatus includes a pulse generator having two piston pairs 531 operating in a common cylinder 532 with 3 isolated chambers and an entrainment pacifier assembly 533 connected to two of the three cylinder chambers. One piston of each of the piston pairs operates in the center chamber 534 of the cylinder. The other piston of each piston pair operates in one of the two end chambers 535, 536 of the cylinder. The cylinder chambers are pneumatically isolated from each other by a chamber wall 537 having a wiper seal about the rod connecting the pistons in each of the piston pairs. Alternating pressure pulses are generated when the piston pairs move simultaneously in opposite directions. For example, a positive pulse is generated when the piston pairs move away from each other. A negative pressure is generated as the pistons move toward each other. A controller 538, with control valves 539 coupled to ports 540, 541 in the center chamber of the cylinder 532, sequence pressurized gas into and out of the center chamber to alternate the movement of the piston pairs for generating pressure pulses.

FIG. 5A shows compressed gas 542 entering the center port 540 and pressurizing the area between the pistons of the first end of the two piston pairs. Simultaneously, pressure is released from the opposite side of each piston in the center chamber thru the ports 541 between the pistons of the first end and the walls 537 separating the center cylinder chamber from the end chambers. The pressurized gas forces the pistons away from each other. The movement decreases the volume of the area between the pistons at the second end of each piston pair and connected with the pacifier assembly. The decreased volume creates a positive pressure in the nipple 543 of the pacifier assembly.

FIG. 5B shows compressed gas entering the end ports of the cylinder and pressurizing the area between the pistons of the first end of the two piston pairs and the walls separating the center chamber from the two end chambers of the cylinder. Simultaneously, pressure is released from the center port of the cylinder. The pressurized gas forces the pistons toward each other. The movement increases the volume of the area between the pistons at the second end of each piston pair and connected through the pacifier assembly. The increased volume eventually will create a negative pressure in the pacifier assembly as the pistons move closer together.

The above description assumes that the system, when balanced at atmospheric pressure, does not have the piston pairs positioned at an extreme limit of travel in either direction. In various embodiments, each chamber is coupled to a feedback transducer to allow closed loop control of the alternating pressure pulses during NNS entrainment therapy. Pressure and vacuum limits are determined in part from the volume of space in the pacifier assembly nipple, corresponding connection tube size and length, and the maximum pressure of the compressed gas supply. Rise and fall times for the pressure pulses are determined in part from the pneumatic flow rate of each pneumatic circuit. Positive pneumatic pressure operates the apparatus. In various embodiments, the apparatus is portable and is designed to use an existing pneumatic pressure source including, but not limited to, compressed air or gas available at many hospitals and clinics or compressed $CO_2$ available in portable canisters for home use, for example. In various embodiments, the apparatus is portable and the controller is powered for periods of time using rechargeable batteries.

Figure 6A:
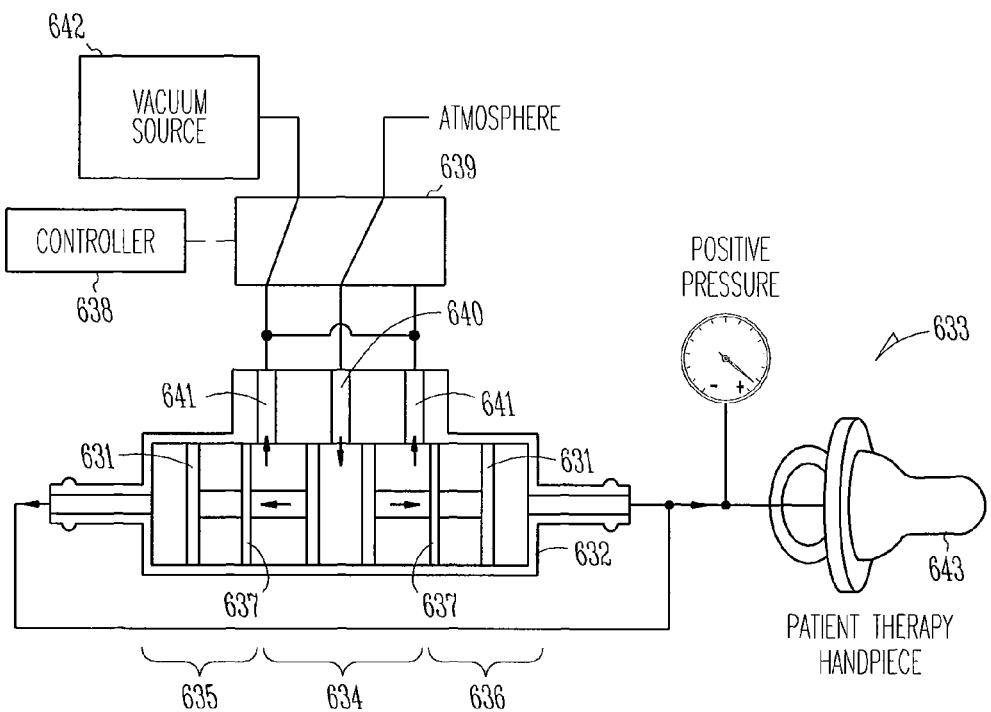
FIGS. 6A and 6B show a NNS entrainment apparatus with a reciprocating piston pulse generator, according to one embodiment of the present subject matter employing a negative pressure source.
Figure 6B:
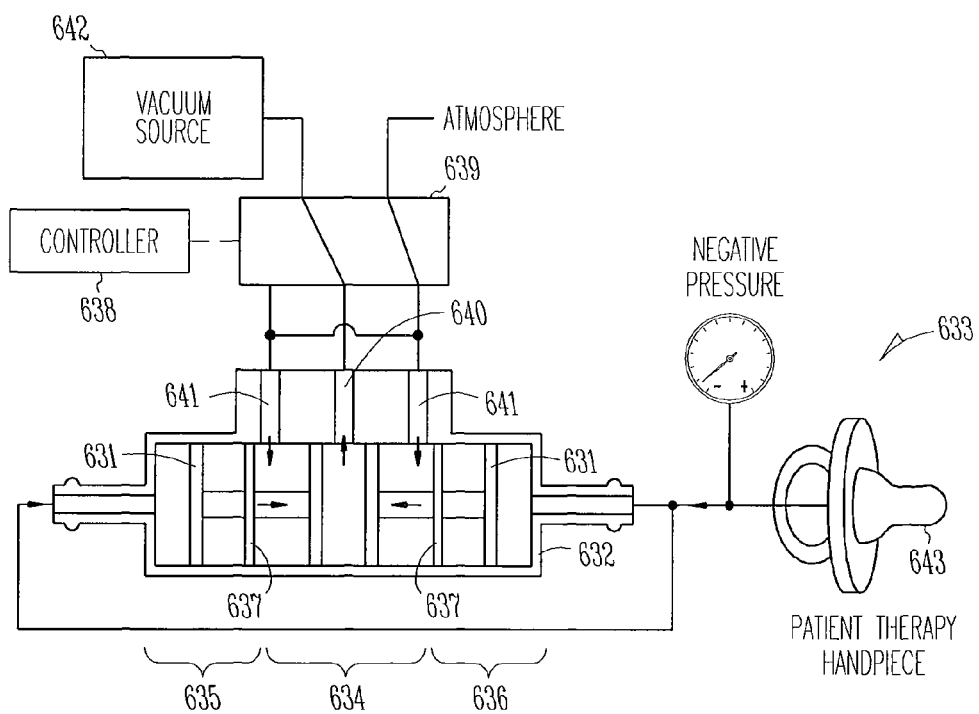

FIGS. 6A and 6B show a NNS entrainment apparatus with a reciprocating piston pulse generator according to one embodiment of the present subject matter employing a negative pressure source. The apparatus includes a pulse generator having two piston pairs 631 operating in a common cylinder 632 with 3 isolated chambers and an entrainment pacifier assembly 633 connected to two of the three cylinder chambers. One piston of each of the piston pairs operates in the center chamber 634 of the cylinder. The other piston of each piston pair operates in one of the two end chambers 635, 636 of the cylinder. The cylinder chambers are pneumatically isolated from each other by a chamber wall 637 having a wiper seal about the rod connecting the pistons in each of the piston pairs. Alternating pressure pulses are generated when the piston pairs move simultaneously in opposite directions. For example, a positive pulse is generated when the piston pairs move away from each other. A negative pressure is generated as the pistons move toward each other. A controller 638, with control valves 639 coupled to ports 640, 641 in the center chamber of the cylinder 632, sequence pressurized gas into and out of the center chamber to alternate the movement of the piston pairs for generating pressure pulses.

FIG. 6A shows a vacuum source 642 applied to the end ports 641 of the cylinder 632, evacuating the area between the pistons of the first end of the two piston pairs 631 and the walls 637 separating the center chamber 634 from the two end chambers 635, 636 of the cylinder. Simultaneously, atmospheric pressure enters the center port 640 of the cylinder 632. The pressure differential forces the pistons away from each other. The movement decreases the volume of the area between the pistons at the second end of each piston pair and connected with the pacifier assembly 633. The decreased volume creates a positive pressure, inflating the nipple 643 of the pacifier assembly 633.

FIG. 6B shows a vacuum source 642 applied to the center port 640 of the cylinder 632 and, evacuating the area between the pistons of the first end of the two piston pairs 631. Simultaneously, atmospheric pressure enters the opposite side of each piston in the center chamber 634 thru the ports 641 between the pistons of the first end and the walls 637 separating the center cylinder chamber 634 from the end chambers 635, 636. The pressurized difference forces the pistons 631 toward each other. The movement increases the volume of the areas between the pistons at the second end of each piston pair. The increased volume, connected through the pacifier assembly 633, creates a negative pressure in the pacifier assembly 633, deflating the nipple 643.

In one example a NNS entrainment pulse generator includes a baglet, a valve assembly in communication with the baglet and with a first pressure and a second pressure, the valve assembly programmable to communicate the first pressure and the second pressure to the baglet to provide pressure changes to the baglet, and a controller coupled to the valve assembly, the controller configured to produce a series of pressure pulses within the baglet.

Variations include but are not limited to, a pump coupled between a first chamber and a second chamber to adjust pressure in each chamber, a first sensor coupled to the first chamber, a second sensor coupled to the second chamber, and first and second pressure valves to couple and decoupled the first and second chambers to the baglet Additional variations include but are not limited to a vent configured to controllably couple the first chamber with atmospheric pressure, an adjustment valve coupled between the first chamber and the second chamber to adjust pressure of the chambers, and a first transducer coupled to the controller and the baglet to sense the pressure within the baglet.

Additional variations include but are not limited to a reciprocating piston assembly comprising a cylinder and a first and second piston slideably disposed within the cylinder, wherein the first piston and the second piston are configured to move in a reciprocating motion.

Additional variations include but are not limited to a valve coupled to the cylinder and configured move the first and second pistons in the reciprocating motion. In some variations, the first pressure is atmospheric pressure. In some variations, the second pressure is positive pressure. In some variations, the second pressure is a negative pressure.

Additional variations include but are not limited to a rechargeable power supply configured to power the controller in a standalone mode and the entire apparatus being portable to reduce patient traffic in hospitals and clinics and to allow home use of a NNS entrainment pulse generator.

In one example, a method includes switching a valve assembly to a first state to generate a positive pressure pulse in a baglet, switching the valve assembly to a second state to generate a negative pressure pulse in the baglet; and repeating the switching of the valve assembly to the first state and the second state to generate a series of pressure pulses in the baglet.

Variations include but are not limited to controllably coupling a positive pressure source directly to the baglet to generate the positive pressure pulse in the baglet, controllably coupling a negative pressure source directly to the baglet to generate the negative pulse in the baglet and producing a pressure pulse waveform comprising pressure pulses having a frequency of about 1.8 Hertz.

Additional variations include but are not limited to controllably coupling a first pressure to a first port of a cylinder of a reciprocating piston assembly, controllably coupling a second pressure to a second port of the cylinder, moving the first and second pistons in a first motion, away from each other, and generating the positive pressure in the baglet using the first motion of the first and second pistons.

Additional variations include but are not limited to controllably coupling the first pressure to the second port of the cylinder, controllably coupling the second pressure to the first port of the cylinder, moving the first and second pistons in a second motion, toward each other, and producing the negative pressure in the baglet using the second motion of the first and second pistons.

Additional variations include but are not limited to controllably coupling a positive pressure to the first port, and controllably coupling a negative pressure to the second port.

Other variations exist and those set forth are intended to demonstrate the present subject matter, but are not exhaustive or exclusive.

This application is intended to cover adaptations and variations of the present subject matter. It is to be understood that the above description is intended to be illustrative, and not restrictive. The scope of the present subject matter should be determined with reference to the appended claims, along with the full scope of legal equivalents to which the claims are entitled.

What is claimed is:

1. A substantially self-contained, non-nutritive suck (NNS) entrainment apparatus, the apparatus comprising:
   a first chamber configured to receive a first pressure;
   a second chamber configured to receive a second pressure;
   a baglet in communication with the first chamber and the second chamber using a valve assembly, the valve assembly controllable to provide pressure changes to the baglet; and
   a controller coupled to the valve assembly, the controller configured to produce a series of pressure pulses within the baglet.

2. The apparatus of claim 1, comprising a pump coupled between the first chamber and the second chamber, the pump configured to reduce pressure in the first chamber and increase pressure in the second chamber to provide the first pressure in the first chamber and the second pressure in the second chamber, wherein the second pressure is greater than the first pressure.

3. The apparatus of claim 2, including a first sensor coupled to the first chamber and a second sensor coupled to the second chamber, wherein the controller is configured to control the first pressure and the second pressure using the first sensor, the second sensor and the pump.

4. The apparatus of claim 2, wherein the valve assembly includes:
a first pressure valve configured to controllably couple and decouple the first chamber to the baglet; and
a second pressure valve configured to controllably couple and decouple the second chamber to the baglet.

5. The apparatus of claim 2, including a vent configured to controllably couple the first chamber with atmospheric pressure.

6. The apparatus of claim 5, including an adjustment valve coupled between the first chamber and the second chamber, wherein the adjustment valve is configured to adjust pressure of the first chamber or the second chamber.

7. The apparatus of claim 1, including a first transducer coupled to the controller and the baglet, the first transducer configured to sense the pressure within the baglet.

8. The apparatus of claim 1, including a reciprocating piston assembly configured to include the first chamber and the second chamber, the reciprocating piston assembly comprising:
a cylinder having a first end and a second end;
a first piston slideably disposed within the cylinder near the first end; and
a second piston slideably disposed within the cylinder near the second end,
wherein the first piston and the second piston are configured to move in a reciprocating motion.

9. The apparatus of claim 8, wherein the valve assembly includes a valve coupled to the cylinder, the valve configured to switch the first and second pressure to the cylinder to move the first and second pistons in the reciprocating motion.

10. The apparatus of claim 8, wherein the first pressure is atmospheric pressure and the second pressure is a positive pressure source relative to atmospheric pressure.

11. The apparatus of claim 8, wherein the first pressure is atmospheric pressure and the second pressure is a negative pressure source relative to atmospheric pressure.

12. The apparatus of claim 1, including a rechargeable power source configured to power the controller in a standalone mode.

13. The apparatus of claim 1, wherein the apparatus is portable.

14. A method for providing non-nutritive suck entrainment, the method comprising:
generating a first pressure in a first chamber;
receiving the first pressure from the first chamber at a baglet;
generating a second pressure in a second chamber;
receiving the second pressure from the second chamber at the baglet;
alternately repeating the receiving of the first and second pressures at the baglet to generate a series of pressure pulses in the baglet, wherein the first pressure is greater than the second pressure, and wherein the first and second chambers are distinct from the baglet.

15. The method of claim 14, wherein:
the receiving the first pressure at the baglet includes coupling the first chamber directly to the baglet to generate positive pressure in the baglet; and
wherein the receiving the second pressure at the baglet includes coupling the second chamber directly to the baglet to generate negative pressure in the baglet.

16. The method of claim 14, wherein alternately repeating the receiving includes producing a pressure pulse waveform comprising pressure pulses having a frequency of about 1.8 Hertz.

17. The method of claim 14, wherein the receiving the first pressure at the baglet includes:
controllably coupling a third pressure to a first port of a cylinder, the cylinder housing a first piston and a second piston;
controllably coupling a fourth pressure to a second port of the cylinder;
moving the first and second pistons in a first motion, away from each other, using the third pressure and the fourth pressure; and
providing the first pressure to the baglet using the first motion of the first and second pistons.

18. The method of claim 17, wherein the receiving the second pressure at the baglet includes:
controllably coupling the third pressure to the second port of the cylinder;
controllably coupling the fourth pressure to the first port of the cylinder;
moving the first and second pistons in a second motion, toward each other, using the third pressure and the fourth pressure; and
providing the second pressure to the baglet using the second motion of the first and second pistons.

19. The method of claim 17, wherein controllably coupling the third pressure includes controllably coupling a positive pressure to the first port.

20. The method of claim 17, wherein controllably coupling the fourth pressure includes controllably coupling a negative pressure to the second port.

* * * * *